(12) United States Patent
Kolic et al.

(10) Patent No.: US 9,943,450 B2
(45) Date of Patent: Apr. 17, 2018

(54) DIAPER CLOSING STRIP AND METHOD AND DEVICE FOR THE PRODUCTION THEREOF

(71) Applicant: LOHMANN-KOESTER GMBH & CO. KG, Altendorf (DE)

(72) Inventors: Ivica Kolic, Heroldsbach (DE); Tobias Grüner, Igensdorf (DE); Florian Hartung, Erlangen (DE)

(73) Assignee: LOHMANN-KOESTER GMBH & CO. KG, Altendorf (DE)

( * ) Notice: Subject to any disclaimer, the term of this patent is extended or adjusted under 35 U.S.C. 154(b) by 59 days.

(21) Appl. No.: 14/762,056

(22) PCT Filed: Feb. 26, 2014

(86) PCT No.: PCT/EP2014/053733
§ 371 (c)(1),
(2) Date: Jul. 20, 2015

(87) PCT Pub. No.: WO2014/131798
PCT Pub. Date: Sep. 4, 2014

(65) Prior Publication Data
US 2015/0313775 A1 Nov. 5, 2015

(30) Foreign Application Priority Data
Feb. 26, 2013 (DE) .................. 10 2013 101 886

(51) Int. Cl.
*A61F 13/62* (2006.01)
*A44B 18/00* (2006.01)
(Continued)

(52) U.S. Cl.
CPC .... *A61F 13/5622* (2013.01); *A61F 13/15756* (2013.01); *A61F 13/5633* (2013.01);
(Continued)

(58) Field of Classification Search
CPC ............ A61F 13/15756; A61F 13/5622; A61F 13/5638; A61F 13/581; A61F 13/62;
(Continued)

(56) References Cited

U.S. PATENT DOCUMENTS 3,932,328 A 1/1976 Korpman
4,043,340 A 8/1977 Cepuritis
(Continued)

FOREIGN PATENT DOCUMENTS

DE 69020991 T2 11/1995
DE 69706473 T2 4/2002
(Continued)

OTHER PUBLICATIONS

International Search Report dated May 16, 2014 in corresponding International PCT Application No. PCT/EP2014/053733, filed on Feb. 26, 2014 (3 pages).

*Primary Examiner* — Lynne Anderson
(74) *Attorney, Agent, or Firm* — Bookoff McAndrews, PLLC (57) ABSTRACT

The invention relates to a diaper closing strip (1), comprising a substrate (2) and a plurality of mechanical closing elements (3) arranged thereon, which mechanical closing elements have a front-side engaging surface and a rear-side fastening surface, wherein an adhesive element (6) is arranged between the substrate (1) and the rear-side fastening surface of each mechanical closing element (3), which adhesive element does not completely cover the rear-side fastening surface of the mechanical closing element (3).

23 Claims, 6 Drawing Sheets

(51) Int. Cl.
*A61F 13/56* (2006.01)
*B32B 37/18* (2006.01)
*B32B 37/12* (2006.01)
*B32B 38/00* (2006.01)
*B32B 37/00* (2006.01)
*A61F 13/58* (2006.01)
*A61F 13/15* (2006.01)

(52) U.S. Cl.
CPC .......... *A61F 13/581* (2013.01); *A61F 13/622* (2013.01); *A61F 13/625* (2013.01); *B32B 37/0046* (2013.01); *B32B 37/1284* (2013.01); *B32B 37/18* (2013.01); *B32B 38/0004* (2013.01); *A44B 18/008* (2013.01); *B32B 2555/02* (2013.01); *Y10T 156/17* (2015.01); *Y10T 428/24802* (2015.01)

(58) Field of Classification Search
CPC .. A61F 13/622; A61F 13/625; A44B 18/0015; A44B 18/0038; A44B 18/008
See application file for complete search history.

(56) References Cited

U.S. PATENT DOCUMENTS

| | | | |
|---|---|---|---|
| 4,585,450 A | 4/1986 | Rosch et al. | |
| 4,710,536 A | 12/1987 | Klingen et al. | |
| 5,019,071 A | 5/1991 | Bany et al. | |
| 5,053,028 A * | 10/1991 | Zoia | A61F 13/581 604/385.21 |
| 5,624,429 A | 4/1997 | Long et al. | |
| 5,897,546 A * | 4/1999 | Kido | A61F 13/581 24/442 |
| 6,142,986 A | 11/2000 | Lord et al. | |
| 6,264,784 B1 * | 7/2001 | Menard | A61F 13/15699 156/164 |
| 6,443,937 B1 * | 9/2002 | Matsushita | A61F 13/625 24/444 |
| 7,125,400 B2 * | 10/2006 | Igaue | A61F 13/49015 2/114 |
| 2004/0236303 A1 | 11/2004 | Igaue et al. | |
| 2007/0039142 A1 * | 2/2007 | Petersen | A61F 13/581 24/448 |
| 2008/0262461 A1 * | 10/2008 | de Dier | A61F 13/15756 604/385.01 |
| 2010/0015386 A1 * | 1/2010 | Baldauf | A44B 18/0011 428/99 |
| 2011/0313389 A1 | 12/2011 | Wood et al. | |
| 2012/0267033 A1 | 10/2012 | Mueller | |

FOREIGN PATENT DOCUMENTS

| | | |
|---|---|---|
| DE | 20 2004 021 382 U1 | 1/2008 |
| DE | 10 2007 036 596 A1 | 2/2008 |
| DE | 10 2007 058 832 A1 | 5/2009 |
| EP | 0 321 232 A1 | 6/1989 |
| EP | 0 755 665 A1 | 1/1997 |
| EP | 0888104 B1 | 9/2002 |
| EP | 1 484 041 A1 | 12/2004 |
| EP | 2 145 555 A1 | 1/2010 |
| EP | 2441421 A1 | 4/2012 |
| EP | 1 635 752 B1 | 8/2012 |

* cited by examiner

DIAPER CLOSING STRIP AND METHOD AND DEVICE FOR THE PRODUCTION THEREOF

This application is a National Stage filing under 35 U.S.C. § 371 of International PCT Application No. PCT/EP2014/053733, filed Feb. 26, 2014, which claims priority to German Patent Application No. DE 10 2013 101 886.6, filed Feb. 26, 2013, the contents of each of which are incorporated by reference herein.

The invention relates to a diaper fastening tape and a method and apparatus for producing same. More precisely, the invention relates to a diaper fastening tape comprising a plurality of mechanical fasteners, and a method and a device for producing same.

U.S. Pat. Nos. 4,585,450, 5,624,429, 6,142,986 and 4,043,340 amongst other documents disclose diaper fastening tapes for fastening diapers such as baby diapers or incontinence pants for example. A diaper is usually equipped with two diaper fastening tapes, each diaper fastening tape being permanently attached to one of the diaper ears respectively in the rear waist region of the diaper. When putting the diaper on a diaper-wearer, the two diaper fastening tapes are guided around the waist of the diaper-wearer to the front waist region of the diaper, where they make a detachable retaining connection to the diaper. According to the prior art, this detachable retaining connection can be achieved both by an adhesive action and by mechanical means or a combination of the two. Hence, for example, EP1 635 752 A1, EP0 321 232 A1 and EP0 755 665 A1 suggest a diaper fastening tape, for which one or more mechanical fasteners are arranged on an adhesive strip in such a way that exposed regions of the adhesive strip can contribute to the retaining action.

A diaper fastening tape must satisfy two opposing requirements. On the one hand, the front waist region must provide a detachable retaining connection that has enough retaining force to prevent the diaper fastening from opening by itself. This self-opening would not only threaten the correct diaper fitting but also risks the leaking of contents already inside the diaper. On the other hand, the detachable connection must be weak enough to enable opening and then reclosing in order to check the contents of the diaper or to adjust the fit of the diaper. A retaining connection for the diaper fastening tape that is too strong might in this case damage the engaged region of the front waist region of the diaper, i.e. the landing zone, which in turn can limit the effectiveness of the landing zone as a result of torn-out material, and can also impede the adhesive or mechanical fasteners on the diaper fastening tape as a result of adhering torn-out scraps of material.

Achieving a suitable retaining connection between diaper fastening tape and landing zone is made particularly difficult by the fact that both elements are usually not aligned flat with one another. Instead, they are in a position which for a fitted diaper must tolerate a certain curvature, namely the curvature of the waist or torso of the diaper-wearer. This curvature is itself not constant but varies with every body movement of the diaper-wearer, which involves an additional strain on the retaining connection.

Tensile forces place an additional strain on the retaining connection between the mechanical fasteners and the landing zone. Such tensile forces act primarily between the rear waist region of the diaper and the front waist region of the diaper, and hence along the extent of the diaper fastening tape. One of the causes of these forces are movements of the diaper-wearer, primarily changes in the posture, such as sitting, squatting or bending forward for example, which increase the girth of the abdomen or waist of the diaper-wearer.

Therefore the object of the invention is to provide a diaper fastening tape which can display a balanced retaining action with respect to the landing zone that is guaranteed in particular even during static or dynamic deformation of the diaper fastening tape or the landing zone, and that can provide a particular resistance to tensile forces acting along the extent of the diaper fastening tape. It is also the object of the invention to provide a method and a device for producing such a diaper fastening tape.

The object is achieved by a diaper fastening tape and a method and a device for producing same as claimed in the independent claims, wherein the dependent claims each illustrate preferred embodiments.

The invention accordingly proposes a diaper fastening tape that comprises a substrate and a plurality of mechanical fasteners arranged thereon. Each of the mechanical fasteners comprises a front engaging surface and a rear attachment surface, and is joined to the substrate by means of arranging between the rear attachment surface thereof and the substrate an adhesive element that does not entirely cover the rear attachment surface of the mechanical fastener. Hence the adhesive element comprises a spatial extent in the plane of the substrate that is less than the spatial extent of the respective mechanical fastener in the plane of the substrate. This means that in a plan view of the substrate, the adhesive element is completely covered by the mechanical fastener attached thereto, with said mechanical fastener extending beyond the adhesive element at at least one boundary.

A method for producing a diaper fastening tape is also proposed, which method comprises the following steps: providing a substrate; providing each of a plurality of mechanical fasteners with an adhesive element on a rear attachment surface; and joining the mechanical fasteners to the substrate by means of the adhesive element. In this method, the respective adhesive element is provided such that it does not completely cover the rear attachment surface of the mechanical fastener.

In addition, the invention proposes a device for producing a diaper fastening tape, which device comprises a substrate feed for providing a substrate; a fastener feed for providing at least one mechanical fastener having a front engaging surface and a rear attachment surface; a coating device for applying adhesive to the rear attachment surface of the at least one mechanical fastener; and a contact-making device for joining the at least one mechanical fastener to the substrate by means of the adhesive. The coating device here comprises a nozzle arrangement having a plurality of nozzle apertures for providing a corresponding number of adhesive elements.

In general, the diaper fastening tape can comprise an attachment region for permanent attachment to the diaper, in particular to the diaper ears, and a user region. The user region is the region that is guided around the waist of the diaper-wearer to the front waist region of the diaper when putting on the diaper, where it makes a detachable retaining connection to the landing zone of the diaper. It comprises in particular the region of the diaper fastening tape on which the plurality of mechanical fasteners are arranged. An intermediate region can be provided between the attachment region and the user region, which intermediate region ensures free movement of the user area and optionally provides the diaper fastening tape with elastic, in particular elastically stretchable, properties. The user region in turn can comprise at its outer boundaries, in particular the boundary opposite the attachment region, a holding region, which itself can have different properties and can be used primarily for handling the diaper fastening tape when putting on and fastening the diaper.

The substrate preferably extends over the entire region of the diaper fastening tape, in particular over the attachment region and the user region. The substrate is a substantially flat entity that extends in the machine direction (MD) and the cross-direction (CD). The plane of the substrate is hence defined by the axes MD and CD (see FIGS. 1 and 2), whereas the thickness of the substrate extends perpendicular to the substrate plane in the direction of the axis Z. Here, the plane of the substrate is therefore understood to mean the plane in which the substrate in the non-deformed state extends along MD and CD.

The term "machine direction" (MD) here denotes the direction of the continuous material of the substrate during the production process. The term "cross-direction" (CD) denotes the direction that runs substantially perpendicular to the machine direction.

The substrate can be formed from a multiplicity of materials or layers, such as paper, film, nonwoven fabric with or without film coating or film-laminated nonwoven fabric for example. These materials are convenient to purchase, easy to process and exhibit advantageous properties such as, for example, good deformability out of the plane of the substrate. A nonwoven fabric with film coating shall be understood to mean here a nonwoven fabric to which a plastic film has been applied on one side. Usually PE polymers, PP polymers or PET polymers are used as the film-coating materials. The coating grammage usually lies between 5 and 40 g/m². Suitable nonwoven fabrics include carded nonwoven fabrics and spunbond fabrics such as those described, for instance, in Albrecht, Fuchs, Kittelmann: Nonwoven Fabrics: Raw Materials, Manufacture, Applications, Characteristics, Testing Processes, Wiley-VCH (2002). Elastic nonwoven fabrics, in particular intrinsically elastic nonwoven fabrics and elastic film-laminated nonwoven fabrics, are also suitable. In addition, materials can comprise single-layer or multilayer films, co-extruded films, laterally laminated films or films containing foamed plastic layers. The layers of such films can themselves be formed from different materials such as, for example, polypropylene, polyvinyl chloride, polyethylene-terephthalate, polyethylene, polyolefin copolymers or blends of polyolefins such as a blend of polypropylene, LPDE (low density polyethylene) and/or LLDPE (linear low density polyethylene) for instance, textiles, foamed materials and nonwoven fabrics.

The thickness of the substrate, i.e. its spatial extent in the direction of the Z-axis, is preferably between 20 and 1000 μm and more preferably between 50 and 200 μm.

The substrate can be divided into a plurality of zones, each zone denoting a different segment of the substrate in the CD, which segment itself has a substantially uniform structure and/or uniform properties. The different zones can be formed from different materials, which can be joined, for example, by means of adhesive such as a self-adhesive bonding agent, ultrasound bonding, thermal bonding, mechanical joining, stapling, or a combination thereof. Different zones can also be produced by activating the material in individual regions, for example by mechanical, thermal, electrical and/or chemical treatment in order to lend different properties or functions to the substrate material.

Preferably, one or more zones of the substrate in the plane of the substrate and in particular in the CD are not deformable, in particular cannot stretch or stretch elastically, with the result that a force acting in the substrate plane and in particular in the CD does not change, or not substantially change, the extent of the relevant zone(s) of the substrate in the substrate plane. For example, the substrate in one or more zones can have a tensile strength in accordance with DIN EN 29073-3 of more than 10 N/50 mm, preferably between 15 and 200 N/50 mm, in particular between 20 and 150 N/50 mm.

The substrate preferably has such properties in the zone that corresponds to the user region of the diaper fastening tape, and in particular in the zone in which the plurality of mechanical fasteners are arranged. The position of the mechanical fasteners relative to one another is hence fixed, i.e. the distance between the mechanical fasteners, in particular in the CD, does not vary or varies only negligibly. Hence the retaining action of the diaper fastening tape with respect to the landing zone exhibits a particular resistance to tensile forces acting along the extent of the diaper fastening tape, in particular in the CD. A possible explanation for this is that by virtue of the described embodiment, said tensile forces are distributed evenly on all the mechanical fasteners, with the result that the retaining forces of the individual mechanical fasteners add up to a total retaining force that is significantly larger than the retaining force of an individual mechanical fastener. Ideally, the total retaining force equals the sum of the retaining forces of the individual mechanical fasteners. If, on the other hand, the substrate can stretch between the mechanical fasteners in the plane of the substrate and in particular in the CD, then the tensile force in the CD could act in the sense of a shear force on the frontmost mechanical fastener in the tensile direction without being transferred to the other mechanical fastener(s) behind said front mechanical fastener. One potential consequence would be that the tensile force in the CD detaches the mechanical fasteners from the landing zone one after the other, whereby the total retaining force in the CD would equal only the retaining force of the frontmost mechanical fastener in the tensile direction. The described preferred embodiment hence helps to improve the detachable retaining connection between diaper fastening tape and landing zone.

Preferably, one or more zones of the substrate are deformable, in particular elastically deformable, in a direction out of the substrate plane. Preferably, the substrate can hence bend, crease and/or curve in the Z-axis direction in the zones concerned, which in particular also includes the substrate rolling up.

More preferably, the substrate comprises good deformability out of the substrate plane, or in other words good deformability in the Z-axis direction, in the zone corresponding to the user region of the diaper fastening tape, and in particular in the zone in which the plurality of mechanical fasteners are arranged, which in particular enables the substrate to be bent, creased, curved or rolled in this region. This deformability enables the diaper fastening tape to adapt to the shape of the landing zone, or in other words the body shape of the diaper-wearer. The resultant dynamic adaptability of the diaper fastening tape to changes in shape of the diaper fastening tape and/or of the landing zone caused by movements of the diaper-wearer is of particular importance here. This also considerably contributes to improving the detachable retaining connection between diaper fastening tape and landing zone.

A plurality of mechanical fasteners are arranged on the substrate. In this context, a plurality means two or more, so for example 2, 3, 4, 5, 6 or 7. By definition, the fasteners are arranged in the substrate region that corresponds to the user region. The user region, however, can extend further than the region in which the fasteners are arranged. In particular, it can comprise further elements or regions that contribute to the detachable retaining connection, such as self-adhesive elements, for example, as disclosed inter alia in documents U.S. Pat. Nos. 4,710,536, 5,019,071 or 3,932,328.

Each of the mechanical fasteners comprises a front engaging surface and a rear attachment surface. The front engaging surface is formed by a plurality of male fastening elements that extend from a supporting layer. The rear of the supporting layer, i.e. the surface of the supporting layer opposite the surface from which the male fastening elements extend, forms the rear attachment surface.

The male fastening elements are suitable for engaging in fibrous materials having a plurality of complementary female fastening elements. Each male fastening element usually comprises a stem, which at one end is joined to the supporting layer of the mechanical fastener, and at the other end comprises a broadened or curved segment. Alternatively, instead of the broadened segment, the stem can comprise a conical, cylindrical, spherical, hemispherical or pyramidal shape.

The broadened segment of a male fastening element can have different shapes, such as, for example, the shape of a hook, a T, a J or a mushroom head, including concave heads or disc-shaped heads, or any other shape that allows the male fastening elements to engage with complementary female fastening elements.

The male fastening elements can be made from a multiplicity of materials, including thermoplastic polymers such as, for example, nylon, polyester, polyolefins, or a combination thereof. The male fastening elements, however, preferably comprise the material from which the supporting layer of the mechanical fastener is made.

The dimensions of an individual male fastening element can vary according to the purpose and according to the structure and composition of the complementary female fastening elements. A male fastening element preferably has a stem of diameter between 10 μm and 250 μm and of length between 40 μm and 2 mm. The broadened region at the end of the stem opposite the supporting layer here preferably comprises a diameter that is larger than the stem diameter by a factor of 1.5 to 5.0.

The male fastening elements are preferably integrally formed with the supporting layer of the mechanical fastener. It is also possible, however, that the male fastening elements are attached to the supporting layer individually or as groups having a common base. Thus individual hooks or groups of hooks can be joined to the supporting layer by adhesive, ultrasound bonding or thermal bonding.

Usually a plurality of male fastening elements are arranged on the supporting surface of the mechanical fastener, typically in a density of $10/cm^2$ to $5000/cm^2$, preferably $200/cm^2$ to $1000/cm^2$. Male fastening elements in such a number thus form the (front) engaging surface of the mechanical fastener.

The supporting layer, the rear of which forms the (rear) attachment surface, can mainly be formed from any thermoplastic material suitable for producing films. Preferred thermoplastic materials include polyesters such as, for example, poly(ethylene terephthalate), polyamides such as, for example, nylon, poly(styrene-acrylonitrile), poly(acrylonitrile butadiene styrene), polyolefins such as, for example, polypropylene and plasticized polyvinyl chloride. The supporting layer can be made of a single material and have a substantially uniform structure in the CD, although it can also comprise a sequence of two or more zones in the CD that have different properties and preferably extend continuously in the MD. The supporting layer can be made of layers of different materials, for example, which are coextruded or laminated on one another. The supporting layer of a mechanical fastener preferably comprises the same material as the male fastening elements attached thereto, and is preferably integrally formed with therewith. It is particularly advantageous if the supporting layer and the male fastening elements located thereon are formed integrally from polyethylene (PE) or polypropylene (PP).

The supporting layer is typically flat and preferably has an average thickness between 10 μm and 1 mm, more preferably between 15 μm and 750 μm, in particular between 20 μm and 500 μm. The thickness is preferably selected such that the supporting layer is thick enough to provide sufficient stability for the male fastening elements attached thereto and in particular to prevent tearing out, yet being thin enough to avoid becoming too rigid, which might impair the processability of the diaper fastening tape and the subsequent comfort when wearing the diaper because of the lack of deformability of the supporting layer.

An adhesive element is located between the substrate and the mechanical fastener, more precisely the rear attachment surface of the mechanical fastener. The adhesive element comprises adhesive, which is preferably selected from heat-seal adhesives, in particular polyolefin-based heat-seal adhesives, HMPSA (hot melt pressure sensitive adhesives) based on natural and synthetic rubber and/or polyacrylate hot melt adhesives. Suitable base polymers for the adhesive include polyamides (PA), polyethylene (PE), amorphous poly-alpha-olefins (APAO), ethylene-vinyl acetate copolymers (EVAC), polyester elastomers (TPE-E), polyurethane elastomers (TPE-U), copolyamide elastomers (TPE-A), styrenic block copolymer elastomer (TPE-S) and resins such as, for example, terpenes, hydrocarbon resins and rosin. The adhesives may be chemically hardening adhesives, reactive hot-melt adhesives, physically hardening adhesives and/or curable adhesives, for instance UV-curable adhesives or thermally curable adhesives. The adhesive is preferably solvent-free and preferably has the property of exhibiting lower viscosity in the heated state than in the cooled state. The lower viscosity in the heated state can guarantee sufficient wetting of the surfaces to be bonded, which may be essential for adhesion of the adhesive. The cooling and/or hardening can achieve the desired bonding action, for example by adhesion or cohesion. The adhesive can hence be suitable for being applied in the heated state to the surfaces to be bonded in order to make the desired adhesive bond upon cooling to room temperature. For this purpose, the surfaces to be bonded can first be pretreated, for example undergo corona pretreatment or flame pretreatment. The adhesive is typically processed between 120 and 220° C., preferably between 140 and 180° C. It is preferably selected such that it is hardened as completely as possible at room temperature, and the exposed adhesives surfaces have just a little or no residual tackiness.

The adhesive element is preferably provided by applying adhesive to the rear attachment surface of the mechanical fastener. This prevents the adhesive from sinking into the substrate material before a sufficient adhesive bond has been made to the respective mechanical fasteners. Such sinking of the adhesive would be especially problematic were the substrate formed from an absorbent material such as, for example, a nonwoven fabric, in particular a nonwoven fabric without film coating. Conversely, such a substrate material absorbs particularly well the adhesive that has already been applied to the mechanical fastener, helping to produce a particularly advantageous join between mechanical fastener and substrate. Thus especially for a combination of absorbent substrate material and non-absorbent fastener material, the method results in a considerable improvement in the bonding action, or in other words a considerable reduction in the amount of adhesive required, compared with conventional methods. Reducing the amount of adhesive results in turn in a smaller amount of hard material being present in the hardened state in the diaper fastening tape, which is beneficial for the deformability and thus the adaptability of the diaper fastening tape to static or dynamic deformations, and hence improves the retaining force thereof with respect to the landing zone. Possible absorbent substrate materials are in this case those materials that absorb the molten heated adhesive away from the material surface into the inside of the material, such as nonwoven fabrics, in particular nonwoven fabrics without film coating, and paper for instance. Non-absorbent materials are those materials that hold the molten heated adhesive on their surface, such as polyethylene (PE) and polypropylene (PP) for instance.

According to the invention, the adhesive element is provided such that it does not completely cover the rear attachment surface of the mechanical fastener. Hence there is no adhesive on at least a portion of at least one outer boundary of the mechanical fastener. The adhesive element preferably does not extend in the CD up to an outer boundary of the mechanical fastener. Thus in particular there is no adhesive on one outer boundary in the CD, preferably on both outer boundaries in the CD, of the mechanical fastener. This makes it easier to guide and/or position the mechanical fastener, in particular in a continuous process. Specifically, this ensures that a guiding and/or positioning aid can touch the mechanical fastener and hence guide and/or position same without coming into contact with adhesive at the same time. This prevents adhesive from contaminating the guiding and/or positioning aid. Hence this dispenses with the laborious removal of adhesive from such guiding and/or positioning aids, in particular when it has already hardened.

Furthermore, it makes it possible for the adhesive element, once the adhesive-coated mechanical fastener is joined to the substrate, to have a spatial extent in the plane of the substrate that is less than the spatial extent of the mechanical fastener in the plane of the substrate. The spatial extent in the plane of the substrate shall be understood to mean here the surface that covers the respective element in the plane of the substrate viewed from the Z-axis direction.

This embodiment has considerable advantages in terms of the deformability of the diaper fastening tape and hence the resultant retaining force with respect to the landing zone. As already explained, the adhesive after hardening can form a region that is substantially rigid and cannot or only moderately be deformed. The regions of the diaper fastening tape that are wetted by adhesive are then an obstacle to a deformability of the diaper fastening tape out of the substrate plane. They hence prevent or reduce the aforementioned advantages associated with the deformability, such as adaptability of the diaper fastening tape to static or dynamic deformations of the landing zone, and the resultant improved retaining action. It is hence necessary per se to keep the adhesive regions as small as possible but large enough to guarantee a sufficiently strong bond between substrate and mechanical fastener to prevent the mechanical fastener from detaching from the substrate.

Furthermore, usually the mechanical fastener has only a low deformability. Limiting the adhesive elements to regions that are completely covered by the fastening element ensures that no extra rigid regions are added to the diaper fastening tape. In addition, this embodiment even helps to reduce the stiffening effect of the mechanical fasteners on the diaper fastening tape. The substrate is specifically not stiffened over the entire spatial extent of the mechanical fastener, in particular in the CD, but only over the spatial extent of the adhesive element, in particular in the CD. Since the adhesive element can produce a spatial separation between substrate and mechanical fastener in the Z-axis direction, and itself stiffens only a smaller proportion of the substrate, in particular in the CD, larger regions of the substrate remain free of stiffening influences, which considerably improves the deformability of the diaper fastening tape in the region which comprises the mechanical fasteners and which hence is crucial to imparting the retaining action with respect to the landing zone.

The size of the adhesive element is selected in this case to guarantee a sufficient bond between substrate and mechanical fastener. Preferably, the spatial extent of the adhesive element in the plane of the substrate equals at least 50%, in particular between 60% and 90%, preferably between 70% and 80%, of the spatial extent of the mechanical fastener in the plane of the substrate. Thus after the adhesive element has been applied to the rear attachment surface of the mechanical fastener and/or after the adhesive-coated mechanical fastener has been bonded to the substrate, preferably at least 50%, in particular between 60% and 90%, preferably between 70% and 80%, of the rear attachment surface of the mechanical fastener is covered by adhesive. In addition, the adhesive element preferably has a thickness, i.e. a spatial extent in the Z-axis direction, that can produce a certain separation between substrate and mechanical fastener in the Z-axis direction. For example, the adhesive element can have a thickness between 1 µm and 1 mm, preferably between 10 µm und 500 µm, in particular between 20 µm und 100 µm.

The method for producing the diaper fastening tape is preferably performed continuously. For this purpose, the substrate can be guided as a continuous material in the machine direction over a contact-making device, for example a pair of rollers arranged horizontally and parallel one above the other. The mechanical fasteners can likewise be fed in an opposite direction to the machine direction as a continuous material above the substrate web, and turned around by means of the upper contact-making roller and brought into contact with the substrate in the machine direction. Before being turned around, the mechanical fasteners can be coated with adhesive, which likewise can be provided continuously by a nozzle arrangement. In a preferred embodiment, the mechanical fasteners are provided as strips that theoretically extend infinitely in the MD. Adhesive is applied to each of the strips continuously in the MD, resulting in an adhesive element that is also shaped as a strip. The adhesive is preferably applied such that the width of the resultant adhesive element in the CD is less than the width of the corresponding mechanical fastener in the CD. The mechanical fastener preferably extends beyond the adhesive element in the CD on at least one side, more preferably on both sides. In one embodiment, the width of the adhesive element in the CD equals at least 50%, in particular equals between 60% and 90%, or between 70% and 80%, of the width of the corresponding mechanical fastener in the CD. The adhesive element is preferably arranged centrally in the CD on the mechanical fastener.

Optionally, the continuous method can additionally include applying one or more (functional) layers, for example by lamination, coating or detachable joining.

The product resulting from the continuous method is a diaper fastening tape of theoretically infinite extent in the MD, which can be wound onto discs or reels. Finishing, i.e. cutting, such an infinite diaper fastening tape in the CD, preferably at intervals along the MD between 2.5 and 5.0 cm, in particular 3.0 to 3.5 cm, produces diaper fastening tapes that are suitable in particular for use in baby and incontinence diapers. This cutting can be performed in any suitable way known to a person skilled in the art, in particular using rotary cutters.

The plurality of mechanical fasteners are preferably provided by a single mechanical fastener being divided into a plurality of mechanical fasteners. This can be done in any suitable way known to a person skilled in the art, for example by cutting or stamping the individual mechanical fastener, in particular using blades, rotary cutters or by contactless cutting such as laser cutting and waterjet cutting for instance. (Contactless) cutting is particularly suitable here for a continuous method in which a plurality of strips of mechanical fasteners result from the single mechanical fastener. Stamping the mechanical fastener, on the other hand, can produce any shapes, such as triangles, circles or rhombuses for instance. The mechanical fastener is preferably divided before it is coated with adhesive. This easily and advantageously ensures that a cutting or stamping device used does not come into contact with adhesive. It is hence possible to prevent contamination of the cutting or stamping device and avoid the associated necessary cleaning of molten or already hardened adhesive. This considerably reduces delays and helps to make the method economic. Nevertheless, the mechanical fastener can also be divided after it is coated with adhesive. Contamination of the cutting or stamping device used can be avoided in this case by not applying the adhesive in those regions in which the mechanical fastener is meant to be divided. This means that the adhesive-coated mechanical fastener is divided, in particular cut or stamped, along adhesive-free regions. This results in a plurality of mechanical fasteners, each having one adhesive element on the rear attachment surface, which adhesive element does not cover the rear attachment surface completely. In a continuous method, a plurality of adhesive tracks can be applied, for example, to a wide strip of the mechanical fastener provided as a continuous material. This initially produces a plurality of strip-shaped adhesive elements that extend on the mechanical fastener along the MD. The mechanical fastener can then be divided along the regions between the strip-shaped adhesive elements.

The dividing lines between the individual strips of the mechanical fasteners do not have to run in a straight line, i.e. they can have, for instance, regular or irregular deviations transverse and longitudinal to the machine running direction. After the cutting process, the mechanical fasteners do not have to be severed by a continuous cut, i.e. they can still comprise webs of non-severed mechanical fastening material.

The adhesive can be applied, in particular in a continuous method, by a coating device comprising a nozzle arrangement having a plurality of nozzle apertures. The nozzle arrangement can comprise a nozzle body and a nozzle lip, in both of which are provided intercommunicating channels. Adhesive introduced into the nozzle body can be carried in the communicating channels to the nozzle lip and can exit the nozzle arrangement here via a plurality of nozzle apertures. The nozzle lip is hence the region of the nozzle arrangement that during application of the adhesive to the mechanical fasteners is in close spatial proximity to the mechanical fasteners and may touch same. Thus the nozzle lip advantageously comprises on a surface a contact region that has particular properties such as resistance to mechanical impact, anti-friction properties, dirt-repellent properties, antistatic properties etc. More preferably, a replaceable contact element having just such properties is provided in the contact region. The nozzle lip can preferably have in the region of each nozzle aperture a recess that extends along the MD, preferably over the entire region of the nozzle lip along the MD. The width of the recess in the CD can equal the diameter of the nozzle aperture in the CD.

The coating device preferably also comprises a guiding aid for guiding one or more mechanical fasteners. This can not only ensure that the adhesive is positioned correctly with respect to the (respective) mechanical fastener, but also that the adhesive is dispensed correctly according to the required spatial extent of the adhesive element. For this purpose, the guiding aid can comprise one or more recesses for guiding a corresponding number of mechanical fasteners. The diameter of the (respective) recess in the CD is here preferably selected such that it corresponds to the width of the (respective) mechanical fastener to be guided therein. The recesses can also be dimensioned such that their depth preferably equals at least 70%, in particular between 70% and 250%, preferably between 80% and 110%, of the height of the mechanical fastener to be guided therein. The guiding aid can preferably comprise a plurality of recesses for guiding a corresponding number of mechanical fasteners, and the nozzle arrangement can comprise a corresponding number of nozzle apertures for applying the adhesive elements. The nozzle apertures are arranged to correspond to the position of the recesses in the guiding aid. The recesses in the guiding aid advantageously ensure that each of the mechanical fasteners is located in a correct position with respect to the respective nozzle at the time the adhesive is applied. The recess has the advantage here that it can prevent a potential movement of a mechanical fastener in three directions. In a preferred arrangement of the guiding aid, these directions are an offset of the mechanical fastener to the left in the CD, to the right in the CD and in the Z-axis direction towards or away from the nozzle aperture. This enables the adhesive to be applied in the correct position and dispensed evenly. In particular, the diameter of each nozzle aperture in the CD can be selected to be less than the diameter of the respective corresponding recess in the guiding aid in the CD. The diameter of the nozzle aperture in the CD is preferably chosen to equal at least 50%, in particular between 60% and 90%, preferably between 70% and 80%, of the diameter of the respective corresponding recess in the guiding aid in the CD. This advantageously enables, in particular in a continuous method, the applied adhesive to cover a corresponding surface of the rear attachment surface of the mechanical fastener.

The guiding aid and the nozzle arrangement can be designed as two separate components. In this case at least one of the two components is configured such that it can be brought into spatial proximity with the other component. The guiding aid can be formed, for instance, from a plate or a block in which recesses exist. The recesses can be dimensioned such that their diameter in the CD equals the width of the respective mechanical fastener in the CD, and their depth preferably equals at least 70%, in particular between 70% and 250%, preferably between 80% and 110%, of the height of the mechanical fastener. The nozzle arrangement in turn can comprise nozzle apertures and optionally allocated recesses in the nozzle lip and in the optional contact element, the respective diameter in the CD of said apertures and recesses being less than the diameter of the recesses in the guiding aid in the CD, preferably at least 50%, in particular between 60% and 90%, preferably between 70% and 80%, of the diameter of the respective corresponding recess in the guiding aid.

The nozzle arrangement and the guiding aid are preferably integrally formed. The nozzle arrangement in this case serves simultaneously to guide the mechanical fasteners and to apply the adhesive in the correct position. This can be done by the nozzle lip and/or the optional contact element containing in addition to the nozzle apertures and the optionally allocated recesses, also recesses to guide the mechanical fasteners. Since a nozzle aperture having an optionally allocated recess is allocated to each recess used as a guiding aid, and the recess for the guiding aid is preferably wider in the CD than the corresponding nozzle aperture or allocated recess, the result is a T-shaped cross-section through nozzle aperture and guiding aid. The depth of the recess used as the guiding aid, i.e. the cross-piece of the T, can be selected here such that it equals at least 70%, preferably between 70% and 250%, preferably between 80% and 110%, of the height of the mechanical fastener used in each case. The nozzle apertures or allocated recesses can in turn have a diameter in the CD that is less than the diameter of the recesses used as the guiding aid, preferably at least 50%, in particular between 60% and 90%, preferably between 70% and 80%, of the diameter of the respective corresponding recess used as the guiding aid. The mechanical fastener can here be held inside the recess by various means, for example by holding the mechanical fastener under tension against the guiding aid or by using an opposing component such as a roller, for example, to press the mechanical fastener into the guiding aid.

The device for producing a diaper fastening tape preferably also comprises a cutting device for cutting the mechanical fasteners, such as, for example, an arrangement of blades or contactless cutting tools such as laser cutting tools or waterjet cutting tools, for instance. It is thereby possible, in particular in a continuous method, to divide a mechanical fastener, whether before or after it is coated with adhesive, into a plurality of mechanical fasteners as described above. Depending on the method to be performed, the optional cutting device is therefore placed advantageously either after the coating device (cutting of the adhesive-coated mechanical fasteners) or before the coating device (cutting of the uncoated mechanical fasteners).

The device for producing a diaper fastening tape is preferably also characterized in that it enables the adhesive element, once the mechanical fastener is joined to the substrate, to have a spatial extent in the plane of the substrate that is less than the spatial extent of the mechanical fastener in the plane of the substrate. In particular this can be achieved by the contact-making device, which brings the mechanical fastener, rear-coated with adhesive, into contact with the substrate, being able to exert a variable pressure. It is thereby possible to press the adhesive-coated mechanical fastener against the substrate with a varying intensity, enabling control not only of the adhesion of the adhesive to the substrate but also of the distribution of the adhesive in the plane of the substrate. The pressure is preferably chosen both to guarantee a sufficient adhesive bond between adhesive and substrate and to guarantee a spatial extent of the adhesive element in the plane of the substrate that is less than the spatial extent of the mechanical fastener in the plane of the substrate. The contact-making device is hence preferably formed as a pair of rollers arranged horizontally and parallel one above the other, of which the reciprocal pressure can be varied.

The invention is described by way of example below with reference to the accompanying figures, in which.

Figure 1:
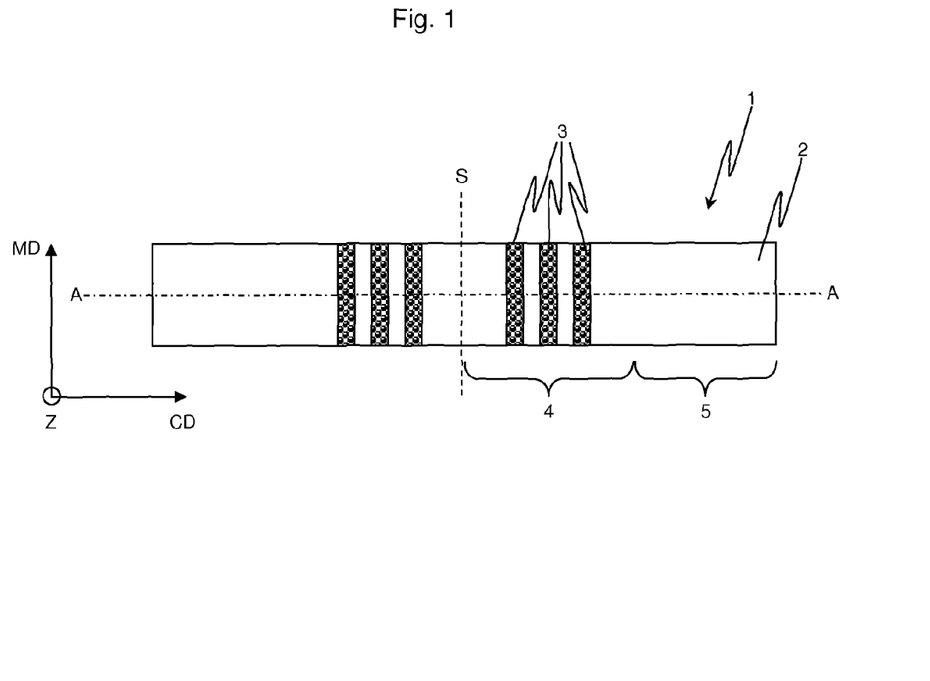
FIG. 1 is a plan view of an exemplary embodiment of a diaper fastening tape according to the invention.

FIG. 1 shows an exemplary embodiment of a diaper fastening tape according to the invention. More precisely, FIG. 1 shows a precursor from which two diaper fastening tapes 1 suitable for fitting to a diaper are obtained by cutting along the line S. Each of these two diaper fastening tapes obtained in this manner comprises a substrate 2, which extends over a user region 4 and a retaining region 5. The substrate 2 is formed from a nonwoven fabric layer, which extends in a plane defined by MD and CD. Mechanical fasteners 3 are arranged on the substrate 2 in the user region 4. Each of the mechanical fasteners 3 covers an underlying adhesive element (not shown), which lies between the mechanical fastener 3 and the substrate 2.

Figure 2:
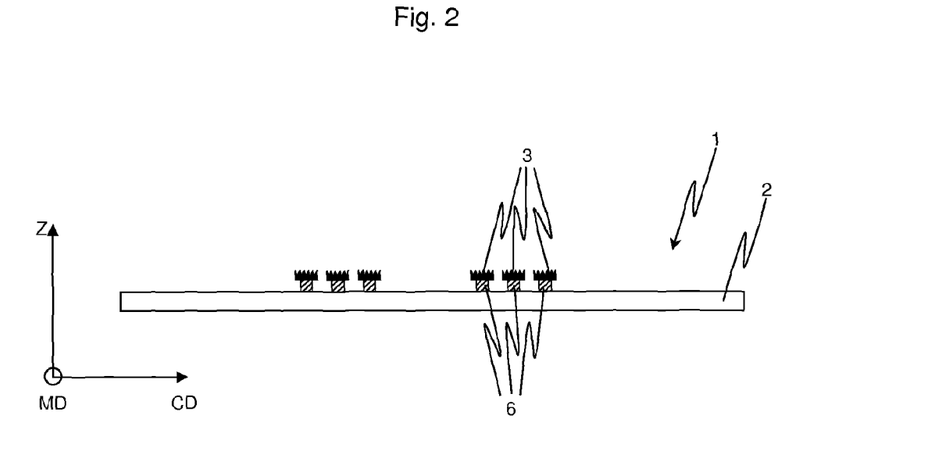
FIG. 2 is a sectional view along the line A-A in FIG. 1.

FIG. 2 is a sectional view along the line A-A in FIG. 1. This figure also shows in addition to the substrate 2 and mechanical fasteners 3, adhesive elements 6 arranged therebetween. The adhesive elements 6 comprise a smaller spatial extent along the CD than the mechanical fasteners.

Figure 3:
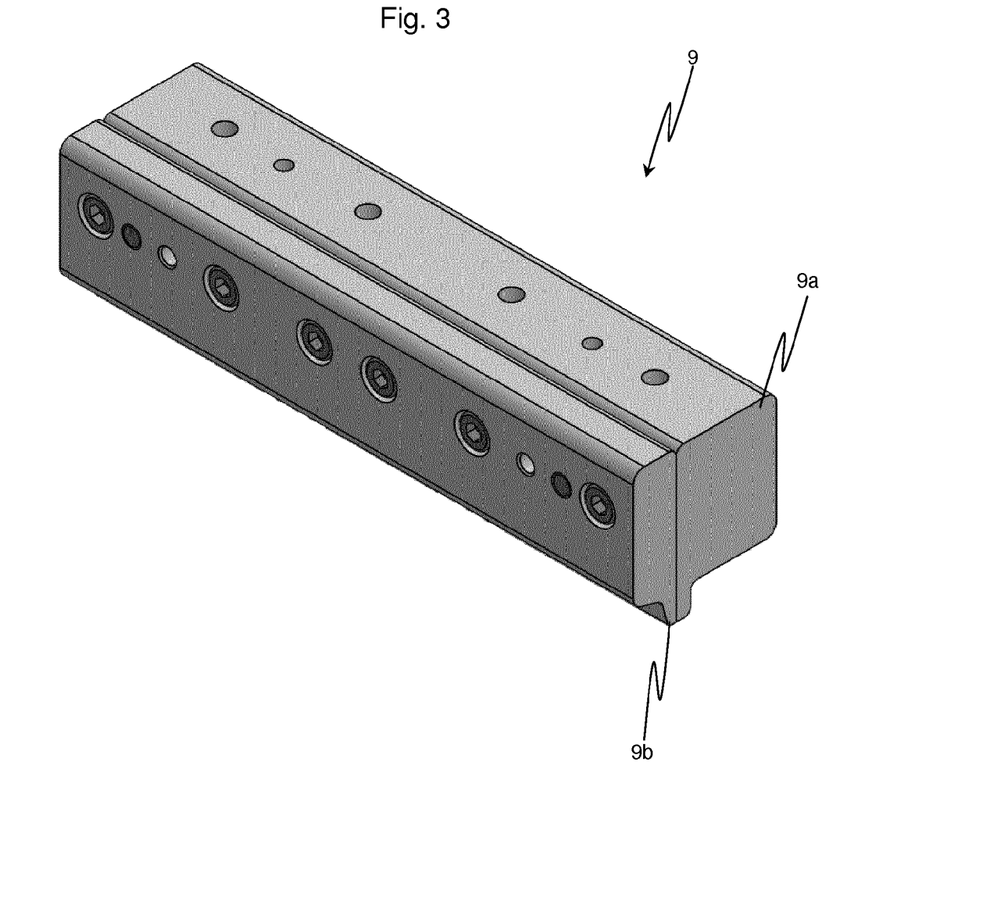
FIG. 3 is a perspective view of an exemplary nozzle arrangement for providing a plurality of adhesive elements.

FIG. 3 shows a perspective view of an exemplary nozzle arrangement 9 for providing a plurality of adhesive elements. The nozzle arrangement 9 comprises a nozzle body 9a and a nozzle lip 9b. In the form shown, the nozzle arrangement 9 is formed from two pieces and can be dismantled along a dividing line running through both the nozzle body 9a and the nozzle lip 9b. Intercommunicating channels (not shown) extend inside the nozzle body 9a and the nozzle lip 9b. Adhesive introduced into the nozzle body can be carried in the communicating channels to the nozzle lip and can exit the nozzle arrangement via a plurality of nozzle apertures.

Figure 4:
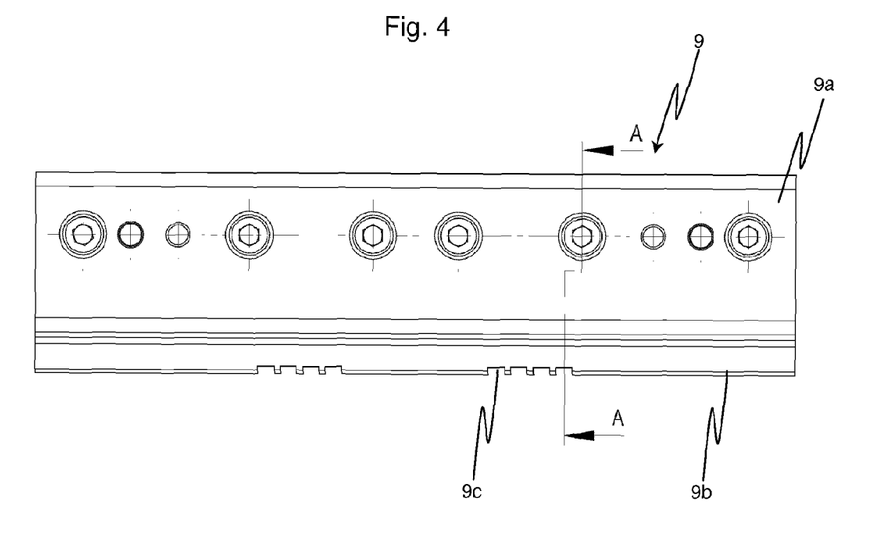
FIG. 4 is a schematic lateral view of the exemplary nozzle arrangement of FIG. 3.

FIG. 4 shows a schematic lateral view of the exemplary nozzle arrangement 9 of FIG. 3, comprising the nozzle body 9a and the nozzle lip 9b. In the lower region of the nozzle lip 9b are recesses 9c, each of which is allocated to a respective nozzle aperture (not shown) and which extend over the full depth of the nozzle lip in the MD.

Figure 5:
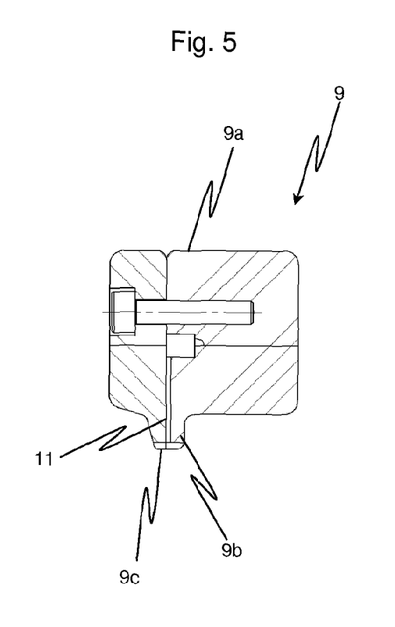
FIG. 5 is a sectional view along the line A-A in FIG. 4.

FIG. 5 shows a sectional view along the line A-A in FIG. 4. It shows the nozzle arrangement 9 comprising the nozzle body 9a and the nozzle lip 9b, and a nozzle 11 formed from a channel that extends through the nozzle body 9a and the nozzle lip 9b. In the lower region of the nozzle lip 9b are recesses 9c, each of which is allocated to a respective nozzle aperture (not shown) and which extend over the full depth of the nozzle lip in the MD.

Figure 6:
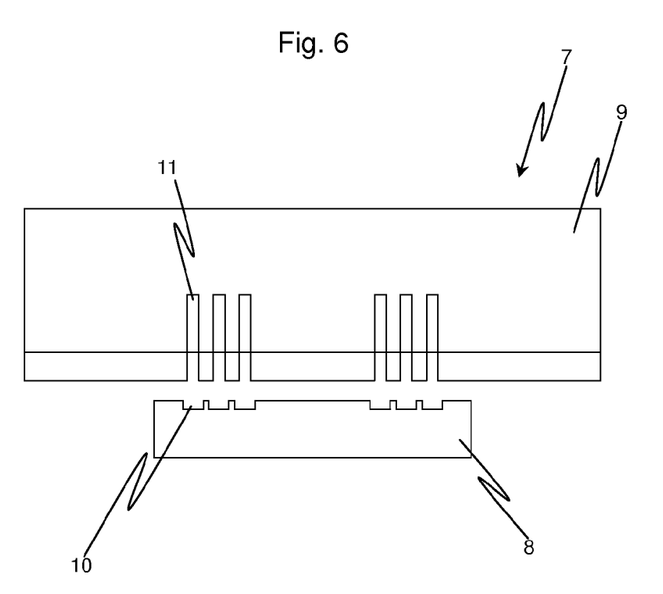
FIG. 6 is a schematic lateral view of a coating device having a guiding aid and a separate nozzle arrangement according to one embodiment of the invention.

FIG. 6 shows an exemplary embodiment of a coating device 7. In the variant shown, this device comprises a guiding aid 8 for guiding mechanical fasteners, and a nozzle arrangement 9. The guiding aid 8 and the nozzle arrangement 9 each comprise recesses 10 and nozzles 11 respectively that correspond with one another, i.e. each recess 10 in the guiding aid 8 is allocated a nozzle 11 in the nozzle arrangement 9. Each recess 10 in the guiding aid 8 has a larger diameter than the corresponding nozzle 11 in the nozzle arrangement 9. The distance between the guiding aid 8 and the nozzle arrangement 9 can be varied. In particular, the guiding aid 8 and the nozzle arrangement 9 can be moved closer together with the result that they make contact or nearly make contact.

Figure 7:
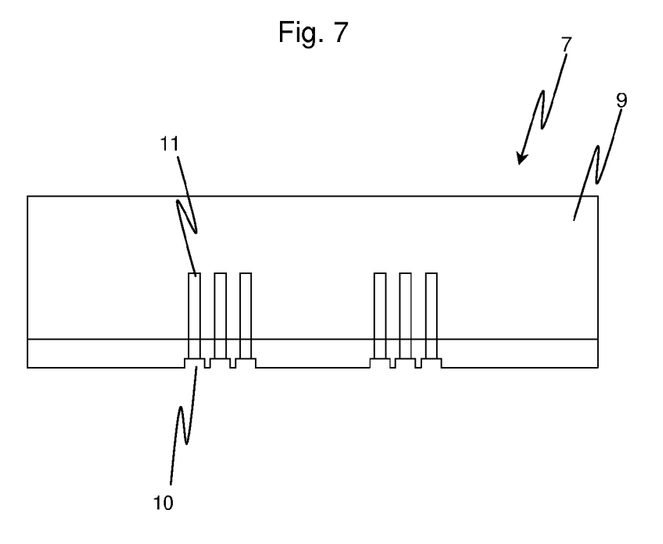
FIG. 7 is a schematic lateral view of a coating device according to a further embodiment of the invention, in which the guiding aid and the nozzle arrangement are integrally formed.

FIG. 7 is a schematic lateral view of a coating device 7 according to a further embodiment of the invention. In this embodiment, the guiding aid 8 and the nozzle arrangement 9 are integrally formed. More precisely, the coating device 7 comprises recesses 10 and nozzles 11 that in cross-section have the shape of a T, where the wider region in each T, i.e. the cross-piece of the T, serves as a guiding aid.

Figure 8:
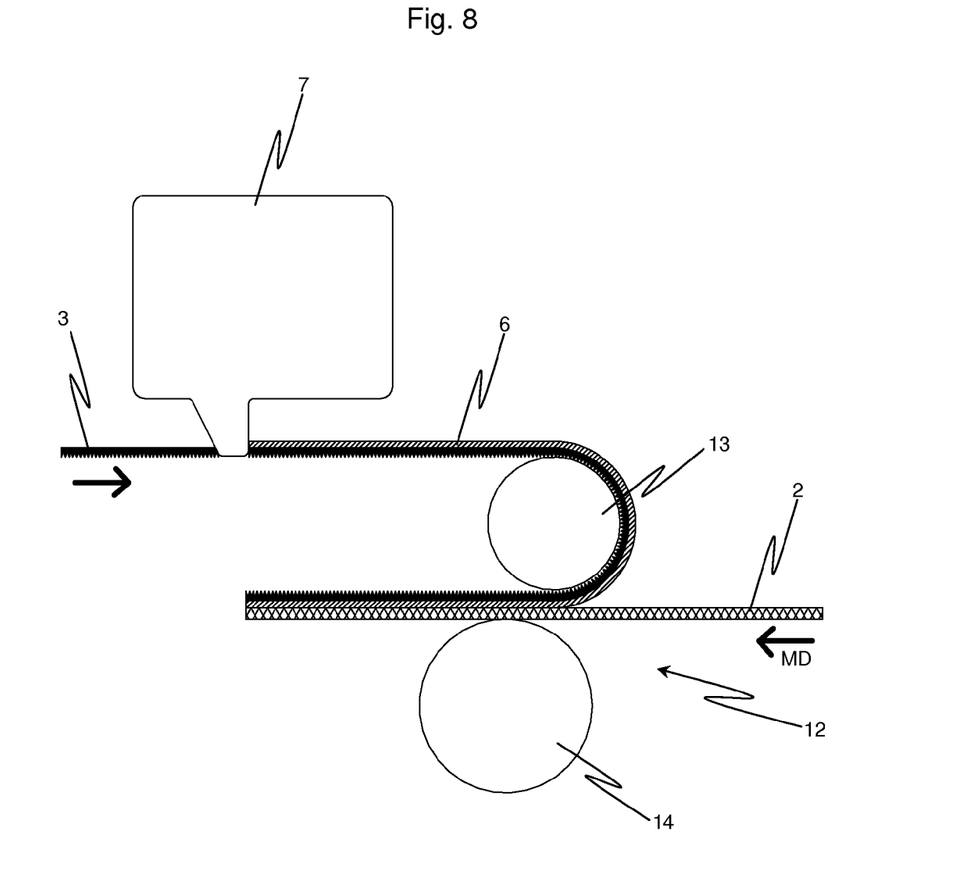
FIG. 8 is a schematic diagram of an exemplary device for producing a diaper fastening tape according to an embodiment of the invention.

FIG. 8 is a schematic diagram of an exemplary device for producing a diaper fastening tape according to an embodiment of the invention. The device comprises a substrate feed for providing the substrate 2, a fastener feed for providing the mechanical fasteners 3, a coating device 7 for applying the adhesive element 6 to the rear attachment surface of each of the mechanical fasteners 3, and a contact-making device 12 for bringing the adhesive-coated mechanical fastener 3 into contact with the substrate 2. The contact-making device 12 comprises a horizontally arranged upper roller 13 and a lower roller 14 arranged parallel thereto. The lower roller 14 carries the substrate 2 in the MD. The mechanical fasteners 3 are fed in an opposite direction to the MD above the substrate web, and turned around by means of the upper roller 13 and brought into contact with the substrate 2 in the machine direction. Before being turned around, the mechanical fasteners 3 are coated with adhesive 6 by the coating device 7.

Figure 9:
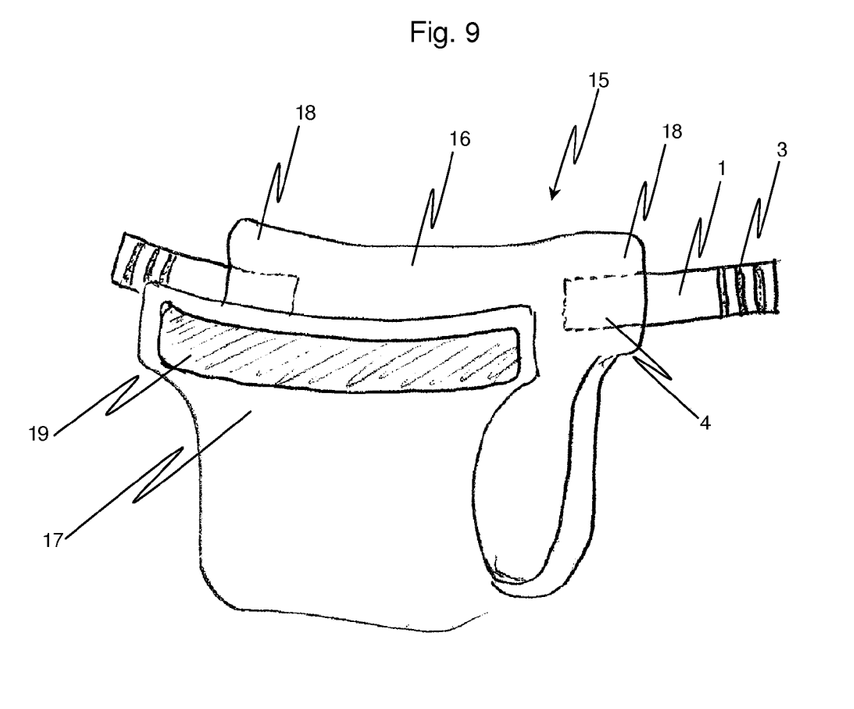
FIG. 9 is a schematic view of a diaper, of which on each diaper ear a diaper fastening tape according to a preferred embodiment of the invention is attached.

FIG. 9 shows a schematic view of a diaper 15 having a rear waist region 16 and a front waist region 17. On each diaper ear 18 thereof is attached a diaper fastening tape 1 according to a preferred embodiment of the invention. Each diaper fastening tape 1 is connected via the attachment region 4 thereof to the diaper ear 18. The front waist region 17 of the diaper 15 comprises a landing zone 19. This landing zone comprises female fastening elements, which can form a detachable retaining connection to the male fastening elements of the mechanical fasteners 3.

The invention has been illustrated by way of example using preferred embodiments. A person skilled in the art will recognize that variants thereof are possible that still lie within the concept forming the basis of the invention. The embodiments shown shall therefore not be understood to limit the scope of protection, which is defined by the accompanying claims.

LIST OF REFERENCES 1 diaper fastening tape
2 substrate
3 mechanical fasteners
4 attachment region
5 user region
6 adhesive elements
7 coating device
8 guiding aid
9 nozzle arrangement; 9a nozzle body; 9b nozzle lip; 9c recesses
10 recess in guiding aid
11 nozzle
12 contact-making device
13 upper roller
14 lower roller
15 diaper
16 rear waist region
17 front waist region
18 diaper ear
19 landing zone

The invention claimed is:

1. A diaper fastening tape comprising a substrate and a plurality of mechanical fasteners arranged thereon, wherein each mechanical fastener has a front engaging surface and a rear attachment surface, wherein the front engaging surface is formed by a plurality of male fastening elements which at one end are directly joined to a supporting layer, and wherein the rear attachment surface is formed by the surface of the supporting layer opposite the surface from which the male fastening elements extend, characterized in that between the substrate and the rear attachment surface of each mechanical fastener a respective adhesive element is arranged that does not entirely cover the rear attachment surface of the mechanical fastener.

2. The diaper fastening tape as claimed in claim 1, characterized in that the substrate in a zone in which the plurality of mechanical fasteners are arranged cannot stretch in the plane of the substrate and/or comprises a tensile strength in accordance with DIN EN 29073-3 of more than 10 N/50 mm.

3. The diaper fastening tape as claimed in claim 1, characterized in that the substrate in the zone in which the plurality of mechanical fasteners are arranged cannot stretch in the cross direction.

4. The diaper fastening tape as claimed in claim 1, characterized in that the substrate in the zone in which the plurality of mechanical fasteners are arranged comprises good deformability out of the substrate plane.

5. The diaper fastening tape as claimed in claim 1, characterized in that the adhesive element covers between 60% and 90% of the rear attachment surface of the mechanical fastener.

6. The diaper fastening tape as claimed in claim 1, characterized in that the mechanical fasteners comprise male fastening elements that extend from a supporting layer.

7. The diaper fastening tape as claimed in claim 1, characterized in that the mechanical fasteners are formed from polyethylene or polypropylene.

8. The diaper fastening tape as claimed in claim 1, characterized in that the adhesive element comprises an adhesive, which is selected from polyolefin-based heat-seal adhesives, HMPSA (hot melt pressure sensitive adhesives) based on natural and synthetic rubber and/or polyacrylate hot melt adhesives.

9. A method for producing a diaper fastening tape as claimed in claim 1, comprising:
    (a) providing a substrate;
    (b) providing of a plurality of mechanical fasteners each with an adhesive element on a rear attachment surface; and
    (c) joining the mechanical fasteners to the substrate by means of the adhesive element;
    characterized in that the respective adhesive element is provided such that it does not completely cover the rear attachment surface of the mechanical fastener.

10. The method as claimed in claim 9, characterized in that the adhesive element is provided such that it covers between 60% and 90% of the rear attachment surface of the mechanical fastener.

11. The method as claimed in claim 9, characterized in that steps a. to c. are performed continuously.

12. The method as claimed in claim 9, characterized in that the providing of the plurality of mechanical fasteners each with an adhesive element on a rear attachment surface in step b is performed by dividing one mechanical fastener into a plurality of mechanical fasteners, in particular by cutting or stamping, and then applying one adhesive element to the rear attachment surface of each of the resultant mechanical fasteners.

13. The method as claimed in claim 9, characterized in that the adhesive element is provided such that it covers between 70% and 80% of the rear attachment surface of the mechanical fastener.

14. A device for producing a diaper fastening tape as claimed in claim 1, comprising: a substrate feed for providing a substrate; a fastener feed for providing at least one mechanical fastener having a front engaging surface and a rear attachment surface; a coating device for applying adhesive to the rear attachment surface of the at least one mechanical fastener; and a contact-making device for joining the at least one mechanical fastener to the substrate by means of the adhesive, characterized in that the coating device comprises a nozzle arrangement having a plurality of nozzle apertures for providing a corresponding number of adhesive elements.

15. The device as claimed in claim 14, characterized in that the coating device also comprises a guiding aid for guiding the at least one mechanical fastener.

16. The device as claimed in claim 15, characterized in that the guiding aid comprises a plurality of recesses for guiding a plurality of mechanical fasteners, wherein each recess in the guiding aid is allocated a corresponding nozzle aperture in the nozzle arrangement.

17. The device as claimed in claim 16, characterized in that each of the nozzle apertures has a diameter in the cross direction that is less than the diameter of the corresponding recess in the guiding aid in the cross direction.

18. The device as claimed in claim 15, characterized in that the guiding aid and the nozzle arrangement are integrally formed.

19. The device as claimed in claim 15, characterized in that the guiding aid and the nozzle arrangement are integrally formed in the form of an assembly having a plurality of T-shaped recesses.

20. A diaper comprising one or more diaper fastening tapes as claimed in claim 1.

21. The diaper fastening tape as claimed in claim 1, characterized in that the substrate in a zone in which the plurality of mechanical fasteners are arranged cannot stretch in the plane of the substrate and/or comprises a tensile strength in accordance with DIN EN 29073-3 between 15 and 200 N/50 mm.

22. The diaper fastening tape as claims in claim 1, characterized in that the substrate in a zone in which the plurality of mechanical fasteners are arranged cannot stretch in the plane of the substrate and/or comprises a tensile strength in accordance with DIN EN 29073-3 between 20 and 150 N/50 mm.

23. The diaper fastening tape as claimed in claim 1, characterized in that the adhesive element covers between 70% and 80% of the rear attachment surface of the mechanical fastener.

\* \* \* \* \*